US00PP24414P2

(12) United States Plant Patent
Bartsch

(10) Patent No.: US PP24,414 P2
(45) Date of Patent: Apr. 29, 2014

(54) ***PETUNIA* PLANT NAMED 'BARTPET001'**

(50) Latin Name: *Petunia×hybrida*
Varietal Denomination: Bartpet001

(75) Inventor: Brian D. Bartsch, Pittsburgh, PA (US)

(73) Assignee: Amerinova Properties LLC, Bonsall, CA (US)

( * ) Notice: Subject to any disclaimer, the term of this patent is extended or adjusted under 35 U.S.C. 154(b) by 66 days.

(21) Appl. No.: 13/507,515

(22) Filed: Jul. 5, 2012

(51) Int. Cl.
*A01H 5/00* (2006.01)

(52) U.S. Cl.
USPC ..... Plt./356.19; Plt./356.1

(58) Field of Classification Search
USPC ..... Plt./356.1, 356.19
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Bartpet001', characterized by its compact and mounding growth habit; freely branching habit; light green and pale yellow variegated leaves; early and freely flowering habit; medium-sized purple violet-colored flowers; and good garden performance.

1 Drawing Sheet

Botanical designation: *Petunia×hybrida*.
Cultivar denomination: 'BARTPET001'.

BACKGROUND OF THE INVENTION

The present invention relates to a new and distinct cultivar of *Petunia*, botanically known as *Petunia×hybrida* and hereinafter referred to by the name 'Bartpet001'.

The new *Petunia* plant is a product of a planned breeding program conducted by the Inventor in Pittsburgh, Pa. The objective of the breeding program is to create new uniform *Petunia* plants with attractive leaf and flower coloration.

The new *Petunia* plant originated from a cross-pollination made by the Inventor in 2008 in Pittsburgh, Pa. of *Petunia×hybrida* 'Shenandoah', not patented, as the female, or seed, parent with an unnamed proprietary selection of *Petunia integrifolia*, not patented, as the male, or pollen, parent. The new *Petunia* plant was discovered and selected by the Inventor as a single flowering plant within the progeny of the stated cross-pollination in a controlled greenhouse environment in Pittsburgh, Pa. in 2009.

Asexual reproduction of the new *Petunia* plant by terminal cuttings in a controlled greenhouse environment in Pittsburgh, Pa. since 2009 has shown that the unique features of this new *Petunia* plant are stable and reproduced true to type in successive generations.

SUMMARY OF THE INVENTION

Plants of the new *Petunia* have not been observed under all possible environmental conditions and cultural practices. The new *Petunia* plant's phenotype may vary somewhat with variations in environmental conditions such as temperature and light intensity without, however, any variance in genotype.

The following traits have been repeatedly observed and are determined to be the unique characteristics of 'Bartpet001'. These characteristics in combination distinguish 'Bartpet001' as a new and distinct *Petunia* plant:

1. Compact and mounding growth habit.
2. Freely branching habit.
3. Light green and pale yellow variegated leaves.
4. Early and freely flowering habit.
5. Medium-sized purple violet-colored flowers.
6. Good garden performance.

Plants of the new *Petunia* can be compared to plants of the female parent, 'Shenandoah'. Plants of the new *Petunia* differ from plants of 'Shenandoah' in the following characteristics:

1. Plants of the new *Petunia* have variegated leaves whereas plants of 'Shenandoah' have solid green-colored leaves.
2. Plants of the new *Petunia* have smaller flowers than plants of 'Shenandoah'.
3. Flowers of plants of the new *Petunia* and 'Shenandoah' differ in flower color as plants of 'Shenandoah' have pink, lavender and white-colored flowers.

Plants of the new *Petunia* can be compared to plants of the male parent selection. Plants of the new *Petunia* differ from plants of the male parent selection in the following characteristics:

1. Plants of the new *Petunia* are more upright than and not as spreading as plants of the male parent selection.
2. Plants of the new *Petunia* have variegated leaves whereas plants of the male parent selection have solid green-colored leaves.

Plants of the new *Petunia* can be compared to plants of the *Petunia* 'USTUN29801', disclosed in U.S. Plant patent application Ser. No. 12/802,249. In side-by-side comparisons conducted in Pittsburgh, Pa., plants of the new *Petunia* differed primarily from plants of 'USTUN29801' in leaf color as plants of 'USTUN29801' had solid green-colored leaves.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical flowering plant of 'Bartpet001' grown in a container.

The photograph at the top of the sheet is a close-up view of typical flowers of 'Bartpet001'.

DETAILED BOTANICAL DESCRIPTION

The aforementioned photographs and following observations, measurements and values describe plants grown in 15.24-cm containers during the late summer and early autumn in a polyethylene-covered greenhouse in Bonsall, Calif. and under commercial cultural practices. During the production of the plants, day temperatures ranged from 27° C. to 35° C., night temperatures ranged from 16° C. to 21° C. and light levels ranged from 8,000 to 10,000 foot-candles. Plants were pinched one time at planting and were eight weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'Bartpet001'.

Parentage:

*Female, or seed, parent.*—*Petunia×hybrida* 'Shenandoah', not patented.

*Male, or pollen, parent.*—Unnamed proprietary selection of *Petunia integrifolia*, not patented.

Propagation:

*Type.*—By terminal cuttings.

*Time to initiate roots, summer.*—About 10 to 14 days at temperatures of about 24° C. to 27° C.

*Time to initiate roots, winter.*—About 14 to 18 days at temperatures of about 18° C. to 24° C.

*Time to produce a rooted young plant, summer.*—About 14 to 21 days at temperatures of about 24° C. to 27° C.

*Time to produce a rooted young plant, winter.*—About 21 to 25 days at temperatures of about 21° C. to 24° C.

*Root description.*—Medium in thickness, fibrous; white in color.

*Rooting habit.*—Freely branching; medium density.

Plant description:

*Plant and growth habit.*—Compact and mounding growth habit; freely branching habit with about five primary lateral branches each with two to three secondary lateral branches developing per plant; pinching enhances lateral branch development; dense and bushy plant form; moderately vigorous growth habit.

*Plant height.*—About 11.5 cm.

*Plant diameter.*—About 23 cm.

Lateral branch description:

*Length.*—About 10 cm.

*Diameter.*—About 2.5 mm.

*Internode length.*—About 1.1 cm.

*Aspect.*—Initially upright to somewhat outwardly spreading.

*Texture.*—Pubescent.

*Color.*—Close to 147C.

Foliage description:

*Arrangement.*—Before flowering, alternate, simple; after flowering, opposite, simple.

*Length.*—About 3.2 cm.

*Width.*—About 2.1 cm.

*Shape.*—Elliptical to obovate.

*Apex.*—Broadly acute to nearly rounded.

*Base.*—Attenuate.

*Margin.*—Entire.

*Texture, upper and lower surfaces.*—Pubescent; viscid.

*Venation pattern.*—Pinnate; arcuate.

*Color.*—Developing leaves, upper surface: Centers, close tp 146C; towards the margins, close to 4C to 4D. Developing leaves, lower surface: Centers, close to 138B; towards the margins, close to 4D. Fully expanded leaves, upper surface: Centers, close tp 138B; towards the margins, close to 4D; venation, close to 138C. Fully expanded leaves, lower surface: Centers, close to 147C; towards the margins, close to 2D; venation, close to 138D.

*Petioles.*—Length: About 5 mm. Diameter: About 2.5 mm. Texture, upper and lower surfaces: Pubescent. Color, upper surface: Close to 145B to 145C. Color, lower surface: Close to 145C.

Flower description:

*Flower arrangement and habit.*—Single-type salver-form flowers; singly arising from leaf axils; freely flowering habit with usually about 20 to 25 flowers developing per plant; flowers face mostly outwardly.

*Fragrance.*—None detected.

*Natural flowering season.*—Plants flower continuously from spring though the autumn in Southern California; plants begin flowering about four to six weeks after planting.

*Flower longevity.*—Individual flowers last about three to four days on the plant; flowers not persistent.

*Flower diameter.*—About 6.4 cm.

*Flower depth (height).*—About 3.4 cm.

*Flower throat diameter.*—About 9 mm to 10 mm.

*Flower tube length.*—About 2.9 cm.

*Flower tube diameter, base.*—About 4 mm.

*Flower buds.*—Shape: Oblong, elongated. Length: About 4 cm. Diameter: About 8 mm. Color: Close to 90D.

*Corolla.*—Arrangement: Five petals fused at the base and opening into a flared trumpet. Petal length from throat: About 2.4 cm. Petal lobe width: About 2.7 cm. Petal shape: Spatulate. Petal apex: Obtuse. Petal margin: Entire. Petal texture, upper surface: Smooth, glabrous; velvety. Petal texture, lower surface: Slightly pubescent along the veins. Throat texture: Smooth, glabrous. Tube texture: Pubescent. Petal color: When opening, upper surface: Brighter than 77A. When opening, lower surface: Close to 90C. Fully opened, upper surface: Slightly darker than N81A; towards the throat, close to 86D; venation, close to 86A. Fully opened, lower surface: Close to N88C; venation, close to N88C. Throat: Close to N87D; venation, close to 79A. Tube: Close to 86C to 86D; venation, close to N79C.

*Calyx.*—Arrangement: One star-shaped calyx tube with five sepals fused at the base per flower. Sepal length: About 1.2 cm. Sepal width: About 3 mm. Sepal shape: Obovate. Sepal apex: Obtuse. Sepal base: Truncate. Sepal margin: Entire. Sepal texture, upper and lower surfaces: Pubescent. Color, upper surface: Close to 1D with random patches, close to 138A. Color, lower surface: Close to 1D with random patches, close to 138B to 138C.

*Peduncles*.—Length: About 2.9 cm. Diameter: About 2 mm. Angle: About 35° from the stem axis. Strength: Strong. Texture: Pubescent. Color: Close to 194B.

*Reproductive organs*.—Stamens: Quantity: Five per flower. Filament length: About 1.7 cm. Filament color: Close to NN155D. Anther shape: Nearly round. Anther size: About 2.5 mm. Anther color: Close to 93C. Pollen amount: Moderate. Pollen color: Close to 96D. Pistils: Quantity: One per flower. Pistil length: About 2.5 cm. Style length: About 1.9 cm. Style color: Towards the apex, close to 86D; towards the base, close to 157D. Stigma shape: Rounded. Stigma color: Close to 146B. Ovary color: Close to 145B. Seeds and fruits: Seed and fruit development have not been observed on plants of the new *Petunia*.

Garden performance: Plants of the new *Petunia* have been observed to have good garden performance and tolerate wind, rain and temperatures ranging from about 5° C. to about 40° C.

Pathogen & pest resistance: Plants of the new *Petunia* have not been observed to be resistant to pathogens and pests common to *Petunia* plants.

It is claimed:

1. A new and distinct *Petunia* plant named 'Bartpet001' as illustrated and described.

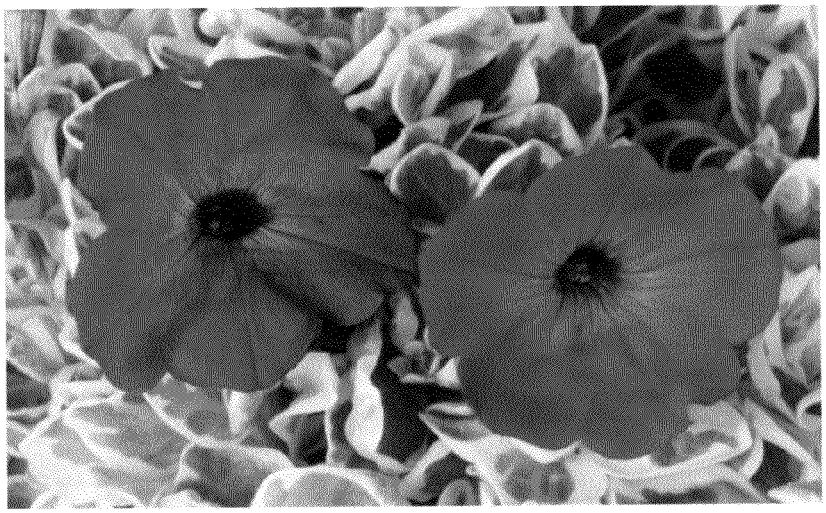
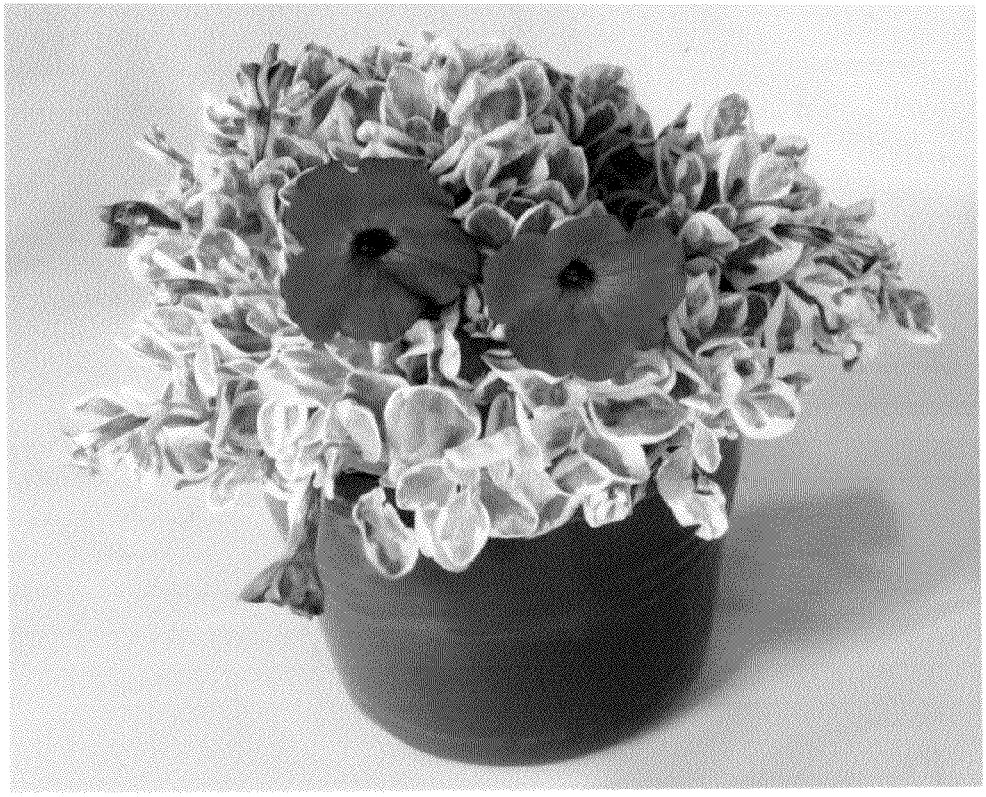

* * * * *